(12) United States Patent
Kim et al.

(10) Patent No.: US 9,659,743 B2
(45) Date of Patent: May 23, 2017

(54) IMAGE CREATING METHOD AND IMAGING SYSTEM FOR PERFORMING THE SAME

(71) Applicant: Samsung Electronics Co., Ltd., Suwon-si, Gyeonggi-do (KR)

(72) Inventors: Jung-Hwan Kim, Pyeongtaek-si (KR); Min-Kook Kim, Goyang-si (KR); Yu-Sin Yang, Seoul (KR); Sang-Kil Lee, Yongin-si (KR); Chung-Sam Jun, Suwon-si (KR)

(73) Assignee: SAMSUNG ELECTRONICS CO., LTD, Gyeonggi-Do (KR)

( * ) Notice: Subject to any disclaimer, the term of this patent is extended or adjusted under 35 U.S.C. 154(b) by 0 days.

(21) Appl. No.: 14/963,654

(22) Filed: Dec. 9, 2015

(65) Prior Publication Data

US 2016/0181061 A1 Jun. 23, 2016

(30) Foreign Application Priority Data

Dec. 18, 2014 (KR) .......................... 10-2014-0182994

(51) Int. Cl.
| H01J 37/22 | (2006.01) |
| H01J 37/21 | (2006.01) |
| H01J 37/285 | (2006.01) |
| H01J 37/31 | (2006.01) |

(52) U.S. Cl.
CPC .......... *H01J 37/222* (2013.01); *H01J 37/285* (2013.01); *H01J 37/31* (2013.01); *H01J 2237/2445* (2013.01)

(58) Field of Classification Search
CPC .... H01J 37/3056; H01J 37/222; H01J 37/256; G01N 23/2202; G01N 23/2251
USPC ......... 250/307, 310, 306, 492.2, 492.3, 305, 250/309, 396 R, 397, 492.21; 382/145, 382/141, 144, 147, 151
See application file for complete search history.

(56) References Cited

U.S. PATENT DOCUMENTS

| 5,616,921 A * | 4/1997 | Talbot .................... B23K 15/02 204/192.33 |
| 7,340,099 B2 | 3/2008 | Zhang |
| 7,483,560 B2 * | 1/2009 | Shishido ............... G06T 7/0004 382/145 |
| 7,889,908 B2 * | 2/2011 | Miyamoto ............ H01J 37/222 250/492.2 |
| 7,947,951 B2 * | 5/2011 | Khursheed .............. H01J 37/05 250/305 |
| 8,229,205 B2 * | 7/2012 | Hyon ........................ G03F 1/84 382/141 |

(Continued)

FOREIGN PATENT DOCUMENTS

| EP | 2688040 A2 | 1/2014 |
| KR | 10-0290026 B1 | 7/2001 |

(Continued)

*Primary Examiner* — David A Vanore
(74) *Attorney, Agent, or Firm* — Harness, Dickey & Pierce, P.L.C

(57) ABSTRACT

A spatial image having 2D spatial information is obtained from a surface of a sample by an image creating method. The surface of the sample is milled to obtain an elemental image having material information from the milled surface. The spatial image and the elemental image are composed to form a 2D spatial/elemental image.

20 Claims, 8 Drawing Sheets

(56) References Cited

U.S. PATENT DOCUMENTS

| | | | | |
|---|---|---|---|---|
| 8,294,183 B2* | 10/2012 | Sakai | .................. | H01L 21/0242 |
| | | | | 257/183 |
| 8,399,831 B2* | 3/2013 | Faber | ..................... | G01N 1/286 |
| | | | | 250/306 |
| 8,716,673 B2* | 5/2014 | Routh, Jr. | ................ | H01J 27/16 |
| | | | | 250/306 |
| 8,933,423 B2* | 1/2015 | Nanri | ..................... | H01J 37/244 |
| | | | | 250/396 R |
| 2009/0135240 A1* | 5/2009 | Phaneuf | ................. | G01N 1/286 |
| | | | | 347/246 |
| 2009/0296073 A1* | 12/2009 | Wagganer | .......... | G01N 23/2202 |
| | | | | 356/72 |
| 2012/0223227 A1* | 9/2012 | Chen | .................. | G01N 23/2251 |
| | | | | 250/307 |
| 2015/0323517 A1* | 11/2015 | Washburn | ............ | G01N 33/246 |
| | | | | 73/73 |

FOREIGN PATENT DOCUMENTS

| | | | |
|---|---|---|---|
| KR | 10-0687414 B1 | | 2/2007 |
| KR | 2007-0032479 A | | 3/2007 |
| KR | 10-0993486 B1 | | 11/2010 |
| WO | WO-2013035082 A1 | | 3/2013 |

\* cited by examiner

52

54

56

60

IMAGE CREATING METHOD AND IMAGING SYSTEM FOR PERFORMING THE SAME

PRIORITY STATEMENT

This application claims priority under 35 U.S.C. §119 to Korean Patent Application No. 10-2014-0182944, filed on Dec. 18, 2014 in the Korean Intellectual Property Office (KIPO), the contents of which are herein incorporated by reference in their entirety.

BACKGROUND

1. Field

Example embodiments relate to an image creating method and/or an imaging system for performing the same. More particularly, example embodiments relate to an image creating method for analyzing a semiconductor structure and/or an imaging system for performing the same.

2. Description of the Related Art

With the trend of miniaturizing semiconductor device dimensions, the use of 3-dimensional (3D) measurement for a complicated semiconductor structure is increasing. A 3D element analysis technology for the semiconductor structure using 3D structural and elemental analysis may be considered as useful.

A 2D elemental analysis technology such as secondary ion mass spectroscopy (SIMS), energy dispersive X-ray spectroscopy (EDX), etc, may have many limits in lateral resolution. Accordingly, there are difficulties in detecting elemental distribution, defects, singularity on cell by using the 2D elemental analysis technology. On the other hand, 2D image technology such as Vertical SEM (VSEM), transmission electron microscopy (TEM), etc, may have a relatively high lateral resolution, however, specimen preparation is time consuming and there are many limits in a real time feedback in aspect of an in-line process monitoring.

SUMMARY

According to at least one example embodiment, an image creating method capable of obtaining a 3D spatial and elemental image of high resolution through 2D resolution improvements of element mapping images is provided.

Some example embodiments provide an imaging system for performing the image creating method.

According to some example embodiments, in an image creating method, a spatial image having 2D spatial information is obtained from a surface of a sample. The surface of the sample is milled to obtain an elemental image having material information from the milled surface. The spatial image and the elemental image are composed to form a 2D spatial/elemental image.

In some example embodiments, the image creating method may include repeatedly performing milling the sample surface along a depth direction of the sample, obtaining the 2D spatial/elemental images with respect to the milled surfaces respectively, and reconstructing the 2D spatial/elemental images to form a 3D spatial/elemental image.

In some example embodiments, obtaining the spatial image may include irradiating an electron beam onto the sample surface, and detecting secondary electrons emitted from the sample surface.

In some example embodiments, obtaining the spatial image may be performed by scanning electron microscope (SEM).

In some example embodiments, obtaining the spatial image may include obtaining a design image of the sample.

In some example embodiments, obtaining the spatial image may include obtaining an elemental image from the sample surface by using energy dispersive X-ray spectroscopy (EDX).

In some example embodiments, milling the surface of the sample may include irradiating an ion beam onto the sample surface, and detecting secondary ions emitted from the sample surface.

In some example embodiments, milling the surface of the sample may be performed using focused ion beam (FIB) or cluster ion beam (CIB).

In some example embodiments, the spatial image may have a first resolution and the elemental image may have a second resolution lower than the first resolution.

In some example embodiments, the sample may include a wafer having a multi-layered structure formed thereon.

According to some example embodiments, in an image creating method, ion milling is repeatedly performed on a surface of a sample along a depth direction to obtain elemental images from the milled surfaces respectively. An electron beam is irradiated on the surfaces to obtain spatial images respectively. The spatial images and the elemental images along the depth direction may be composed to form a plurality of 2D spatial/elemental images. The 2D spatial/elemental images are reconstructed to form a 3D spatial/elemental image.

In some example embodiments, obtaining the spatial image may be performed by scanning electron microscope (SEM).

In some example embodiments, obtaining the spatial image may also include obtaining an elemental image from the sample surface by using energy dispersive X-ray spectroscopy (EDX).

In some example embodiments, milling the surface of the sample may be performed using focused ion beam (FIB) or cluster ion beam (CIB).

In some example embodiments, the spatial image may have a first resolution and the elemental image may have a second resolution lower than the first resolution.

According to some example embodiments, an imaging system includes an electron microscope irradiating an electron beam onto a surface of a sample to obtain a spatial image having 2D spatial information from secondary electrons emitted from the sample surface, a secondary ion mass spectroscope performing ion milling the surface of the sample along a depth direction of the sample to obtain an elemental image having material information from the milled surface, and an image processing part configured to compose the spatial image and the elemental image to form a 2D spatial/elemental image and reconstruct the 2D spatial/elemental image in the depth direction form a 3D spatial/elemental image.

In some example embodiments, the electron microscope may include a scanning electron microscope (SEM).

In some example embodiments, the imaging system may further include an energy dispersive X-ray spectroscope (EDX) which is installed in the electron microscope to detect X-rays emitted from the sample surface onto which the electron beam is irradiated, to obtain an elemental image of the sample surface.

In some example embodiments, the energy dispersive X-ray spectroscope may include an ion beam column irradiating focused ion beam (FIB) or cluster ion beam (CIB).

In some example embodiments, the spatial image may have a first resolution and the elemental image may have a second resolution lower than the first resolution.

According to some example embodiments, in an image creating method, an ion milling may be repeatedly performed to form 2D plan surfaces of a high depth resolution along a depth direction, a spatial image and an elemental image may be obtained from each of the milled surfaces and reconstructed into a high-resolution 3D image.

Thus, the elemental image obtained by SIMS or EDX may be composed with the spatial image such as the SEM image of a relatively high resolution to obtain a high-resolution spatial/elemental image and reconstruct along a depth direction into a 3D spatial and elemental image.

In some example embodiments, an image creating method is provided. The image creating method includes ion milling a surface of a sample to obtain elemental image from the milled surface, irradiating an electron beam on the surface to obtaining a spatial image, composing the spatial image and the elemental image along a depth direction to form a 2D spatial/elemental image, and reconstructing the 2D spatial/elemental image to form a 3D spatial/elemental image.

In at least one example embodiment, the irradiating is performed by a scanning electron microscope (SEM). The irradiating may also include obtaining an elemental image from the sample surface using energy dispersive X-ray spectroscopy (EDX).

In some example embodiments, the ion milling is performed using focused ion beam (FIB) or cluster ion beam (CIB). The spatial image has a first resolution and the elemental image has a second resolution lower than the first resolution.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION OF EXAMPLE EMBODIMENTS

Figure 1:
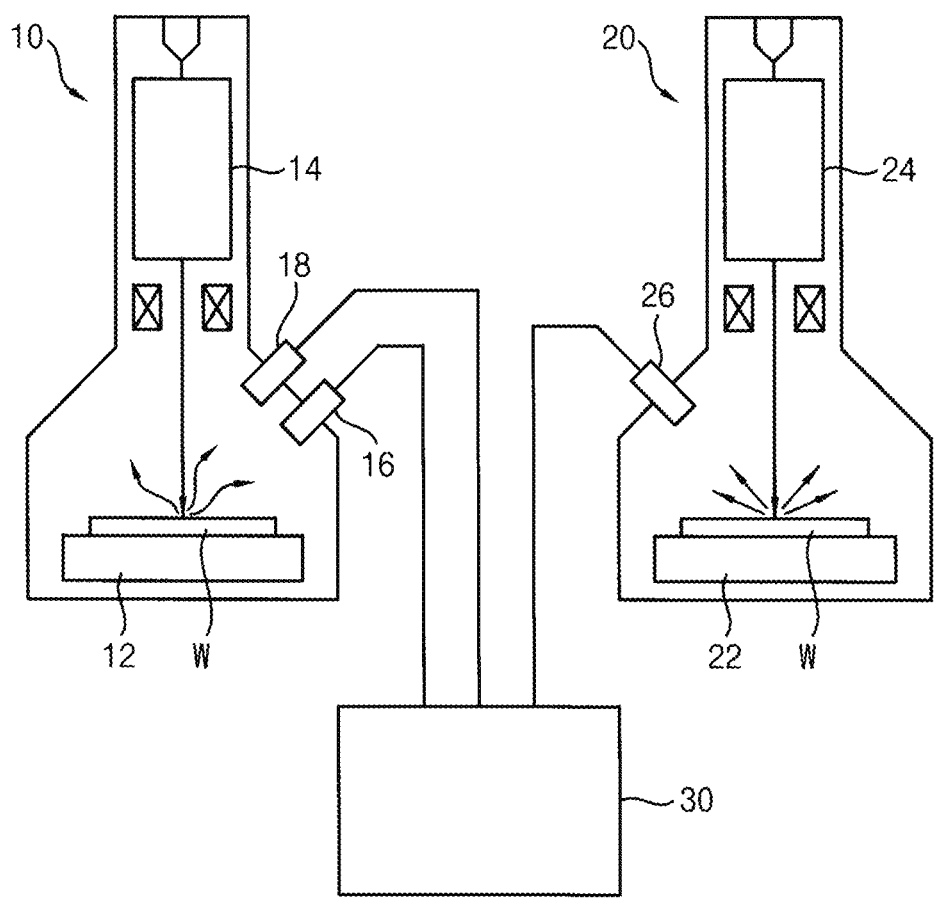
FIG. 1 is a view illustrating an imaging system in accordance with some example embodiments.

Various example embodiments will be described more fully hereinafter with reference to the accompanying drawings, in which example embodiments are shown. Example embodiments may, however, be embodied in many different forms and should not be construed as limited to example embodiments set forth herein. Rather, these example embodiments are provided so that this disclosure will be thorough and complete, and will fully convey the scope of example embodiments to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative teams are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, example embodiments will be explained in detail with reference to the accompanying drawings.

Figure 2:
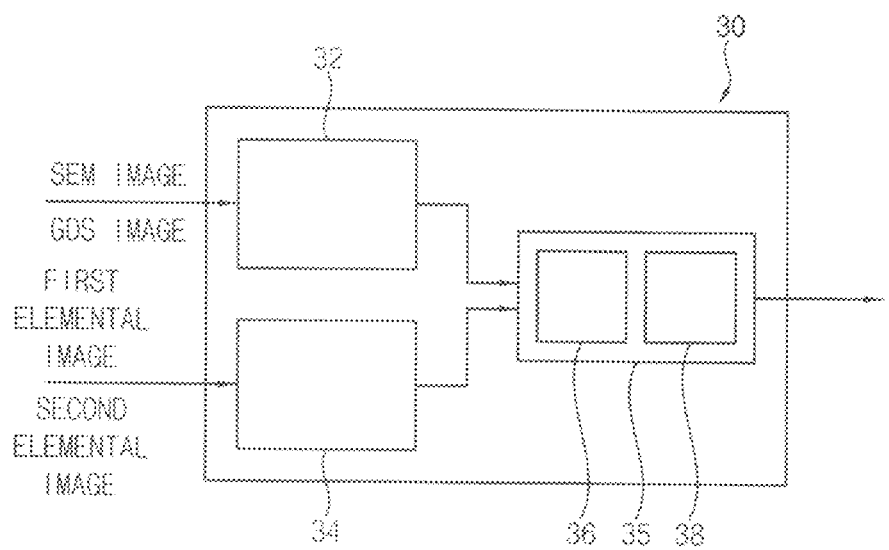
FIG. 2 is a block diagram illustrating an image processing part in FIG. 1.
Figure 3:
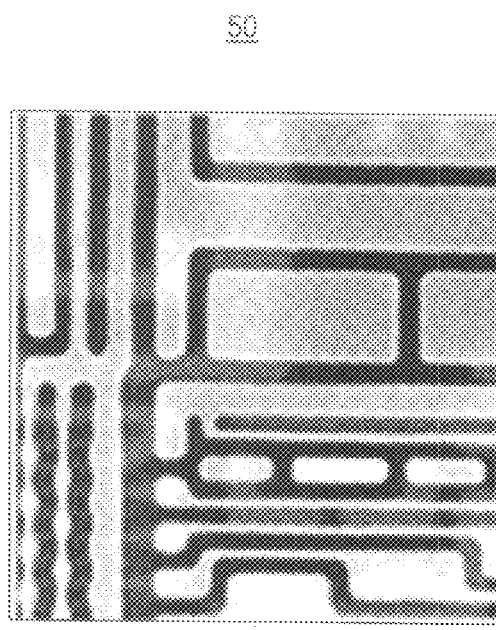
FIG. 3 is a view illustrating a spatial image obtained by an electron microscope in FIG. 1.
Figure 4A:
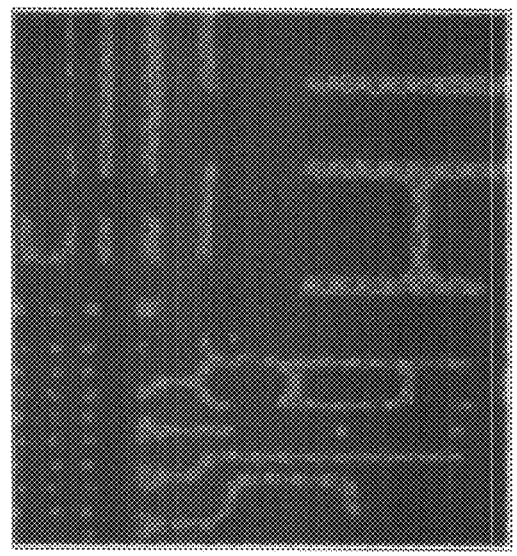
FIGS. 4A to 4C are views illustrating elemental images obtained by a composition analyzer in FIG. 1.
Figure 4B:
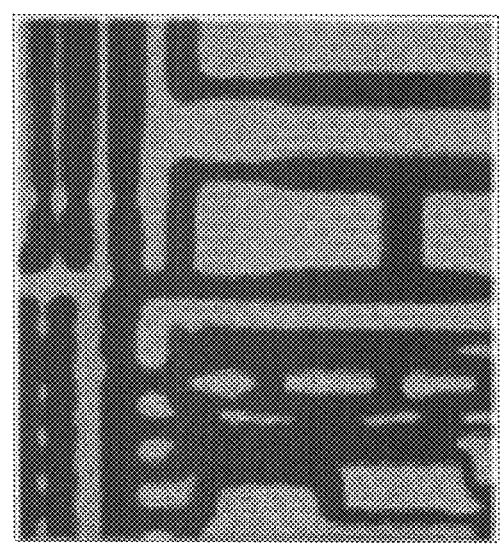
Figure 4C:
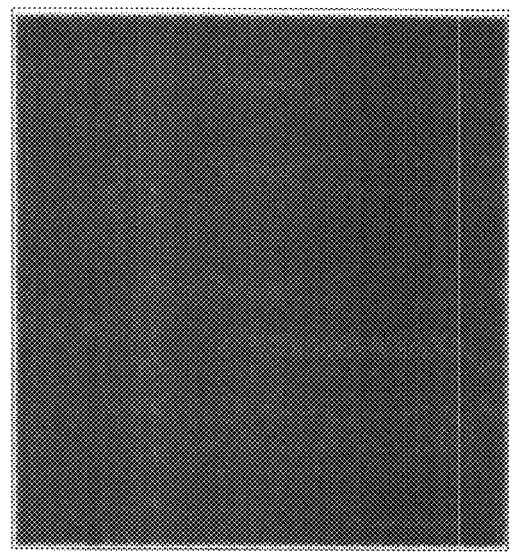
Figure 5:
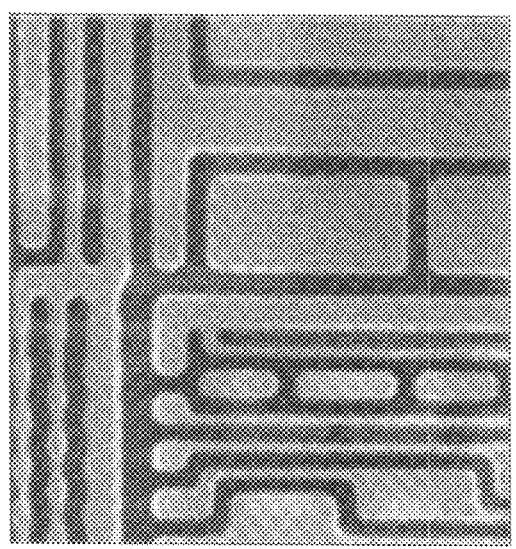
FIG. 5 is a view illustrating a spatial/elemental image obtained by the image processing part in FIG. 1.

FIG. 1 is a view illustrating an imaging system in accordance with some example embodiments. FIG. 2 is a block diagram illustrating an image processing part in FIG. 1. FIG. 3 is a view illustrating a spatial image obtained by an electron microscope in FIG. 1. FIGS. 4A to 4C are views illustrating elemental images obtained by a composition analyzer in FIG. 1. FIG. 5 is a view illustrating a spatial/elemental image obtained by the image processing part in FIG. 1.

Referring to FIGS. 1 to 5, an imaging system may include a structural analysis imaging apparatus configured to obtain a spatial image from a surface of a sample such as a wafer W, an elemental analysis imaging apparatus configured to perform an ion milling on the surface of the sample along a depth direction to obtain an elemental image from the ion beam milled surface, and an image processing part 30 configured to compose the spatial image and the elemental image to form a 2-dimensional (2D) spatial/elemental image and reconstruct a 3-dimensional (3D) spatial/elemental image.

In some example embodiments, the structural analysis imaging apparatus may include scanning electron microscope (SEM), and the elemental analysis imaging apparatus may include a secondary ion mass spectroscope (SIMS), an energy dispersive X-ray spectroscope (EDX), etc. The imaging system may use an ion milling technology to form plan 2D surfaces along a depth direction having a high depth resolution, obtain a spatial image and an elemental image from each of the ion beam milled surfaces and reconstruct the images into a 3D image having a high resolution.

Thus, the elemental image obtained by SIMS or EDX and having a relatively low resolution and sensitivity may be composed with a SEM image having a relatively high resolution using 3D element tomography to detect an element distribution, defects, singularity, etc. on a cell region, to thereby in-line process monitoring semiconductor processes for manufacturing semiconductor devices such as DRAM, VNAND, etc.

As illustrated in FIG. 1, the structural analysis imaging apparatus may include an electron microscope 10 for imaging a sample such as a wafer W having a multi-layered structure formed thereon.

In particular, the electron microscope may include a first stage 12 for supporting the wafer W, and an electron beam column 14 having an electron gun for generating primary electron beam and an electron optical system for controlling a direction and a width of the primary electron beam and irradiating the electron beam onto the wafer W. The structural analysis imaging apparatus may further include a first detector 16 for detecting electrons emitting from the wafer W.

For example, the sample may be a semiconductor wafer including a multi-layered structure formed thereon. The wafer may refer to a substrate formed of a semiconductor or non-semiconductor material. The wafer may include one or more layers formed on the substrate. For example, such layers may include, but may not be limited to, a resist, a dielectric material or a conductive material.

In some example embodiments, an acceleration voltage of the electron beam generated by the electron gun may be adjusted into high voltage or low voltage to control a depth to which the electron beam penetrates into the sample. For example, the electron microscope may include high resolution scanning electron beam (HRSEM) irradiating an electron beam having a high acceleration voltage. When the electron beam is irradiated onto the sample, secondary electrons, backscattered electrons, auger electrons, etc. may emit from the sample.

The first detector 16 may mainly detect the secondary electrons and the backscattered electrons, to thereby obtain a SEM image representing the sample surface. The SEM image may be a spatial image having 2D spatial information. That is, the SEM image may represent a structure of the multi-layers formed on the sample. For example, the first detector 16 may obtain an actual image representing a hole pattern such as contact hole of high aspect ratio.

In addition, a second detector 18 such as EDX may be installed in the electron microscope 10 to detect X-rays emitted from the sample surface onto which the electron beam is irradiated, to obtain an elemental image of the sample surface.

The elemental analysis imaging apparatus may include a secondary ion mass spectroscope (SIMS) 20 as well as EDX installed in the electron microscope 10. The SIMS 20 may irradiate an ion beam on a sample surface and collect secondary ions ejected from an ion beam milled surface of the sample along a vertical depth direction of the sample surface to obtain an elemental image having material property information. The SIMS 20 may include a second stage 22 for supporting the wafer W, and an ion beam column 24 irradiating an ion beam onto a surface of the wafer W to perform an ion milling.

The ion beam column 24 may include an ion gun for generating primary ion beam, and an ion optical system for controlling a direction and a width of the primary ion beam and irradiating the ion beam onto the wafer W. For example, the ion beam column may irradiate focused ion beam (FIB) or cluster ion beam (CIB) onto the sample surface. The elemental analysis imaging apparatus may further include a third detector 26 for detecting ions emitting from the wafer W.

In some example embodiments, the ion beam column 24 may use a low melting metal having low reactivity as an ionic source. Examples of the ionic source may be Al, As, Au, Be, Bi, Cs, Cu, Ge, In, L, Ni, Pb, Pd, Pr, Pt, Zn, etc. For example, the ion beam column 24 may vaporize solid Ga source to be ionized into Ga+ ions and accelerate the Ga+ ions to a desired acceleration voltage. For example, the ion gun may generate an ion beam having an acceleration voltage of about 30 keV or more.

When the ion beam is irradiated onto the sample to ion mill the sample surface to a vertical depth, secondary ions, secondary electrons, etc, may emit from the ion beam milled surface of the sample. A current of the ion beam current and an incidence angle of the ion beam may be adjusted to control a speed of milling the surface, a surface damage, a depth resolution, etc.

The ion beam milling may be one of ion sputtering technologies. In some example embodiments, before the ion beam is irradiated onto the sample, in order to planarize an uneven surface of a 3D semiconductor structure, a material may be formed to fill a gap between patterns. In addition, an ion beam marker may be formed in a region of interest (ROI) such that an image matching may be easily performed without being affected by a limit of a focus depth.

In some example embodiments, the spatial image obtained by the structural analysis imaging apparatus may have a first resolution, and the elemental image obtained by the elemental analysis imaging apparatus may have a second resolution lower than the first resolution. The spatial image may be a black and white image, and the elemental image may be a black and white image or a color image.

The imaging system may be a dual beam system having SEM and FIB. Accordingly, in one chamber, SEM may be used to obtain a spatial image and ion milling with FIB may be performed to obtain an elemental image.

The imaging system may include the image processing part 30 which composes the spatial image and the elemental image to form a 2D spatial/elemental image and reconstruct a plurality of the 2D spatial/elemental images along a depth direction to form a 3D spatial/elemental image.

As illustrated in FIG. 2, in some example embodiments, the image processing part 30 may include a first storage portion 32 storing a spatial image of the sample surface, a second storage portion 34 storing the elemental image of the milled surface of the sample, and an image creation portion 35 composing the spatial image and the elemental image and reconstructing the composed images into the 3D spatial/elemental image.

As illustrated in FIG. 3, the first storage portion 32 may store a SEM image 50 outputted from the first detector 16 of the electron microscope 10. The SEM image 50 may be a 2D spatial image of a pattern formed on the sample surface in ROI.

Additionally, the first storage portion 32 may receive a design image for the pattern formed on the sample surface from a data storage portion (not illustrated). The design image may be a data image for determining a layout of a pattern. For example, the design image may include a graphic data system (GDS) image as a storage format of layout. The GDS image and the SEM image may provide a spatial image having 2D spatial information of the sample surface.

As illustrated in FIGS. 4A to 4C, the second storage portion 34 may store at least one elemental image 52, 54, 56. The second storage portion 34 may store at least one elemental image outputted from the third detector 25 of SIMS 20. Additionally, the second storage portion 34 may store an elemental image outputted from EDX such as the second detector 18. The elemental images 52, 54, 56 may be chemical characterization images having material information of the sample surface. The elemental image may have a resolution lower than a resolution of the spatial image.

The image creation portion 35 may include an image composer 36 composing the spatial image and the elemental image to form a 2D spatial/elemental image and an image reconstructor 38 reconstructing the 2D spatial/elemental images in a depth direction of the sample surface form a 3D spatial/elemental image.

As illustrated in FIG. 5, the image composer 36 may compose the SEM 50 of FIG. 3 and the elemental images 52, 54, 56 of FIGS. 4A to 4C to form a 2D spatial/elemental image 60 at each depth from the sample surface. The image composer 36 may form a plurality of 2D spatial/elemental images along a depth direction, and the image reconstructor 38 may reconstruct the 2D spatial/elemental images obtained at respective depths to form a 3D spatial/elemental image having a relatively high resolution.

As mentioned above, the image system may perform an ion milling to form 2D plan surfaces along a depth direction, obtain a spatial image and an elemental image from each of the milled surfaces and reconstruct them into a high-resolution 3D image.

Thus, the elemental image of a relatively low resolution and sensitivity obtained by SIMS or EDX may be composed with the spatial image such as the SEM image of a relatively high resolution to obtain a high-resolution spatial/elemental image and reconstruct along a depth direction into a 3D spatial/elemental image.

Hereinafter, a method of creating a 3D image of a multi-layered structure formed on a wafer using the imaging system will be explained.

Figure 6:
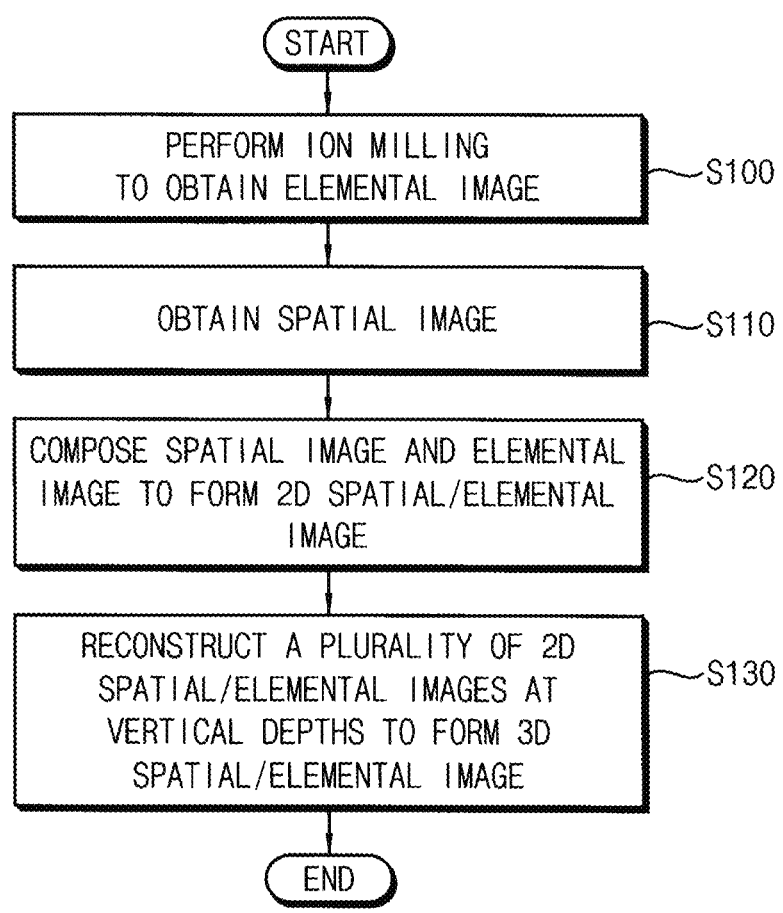
FIG. 6 is a flow chart illustrating an image creating method in accordance with some example embodiments.
Figure 7:
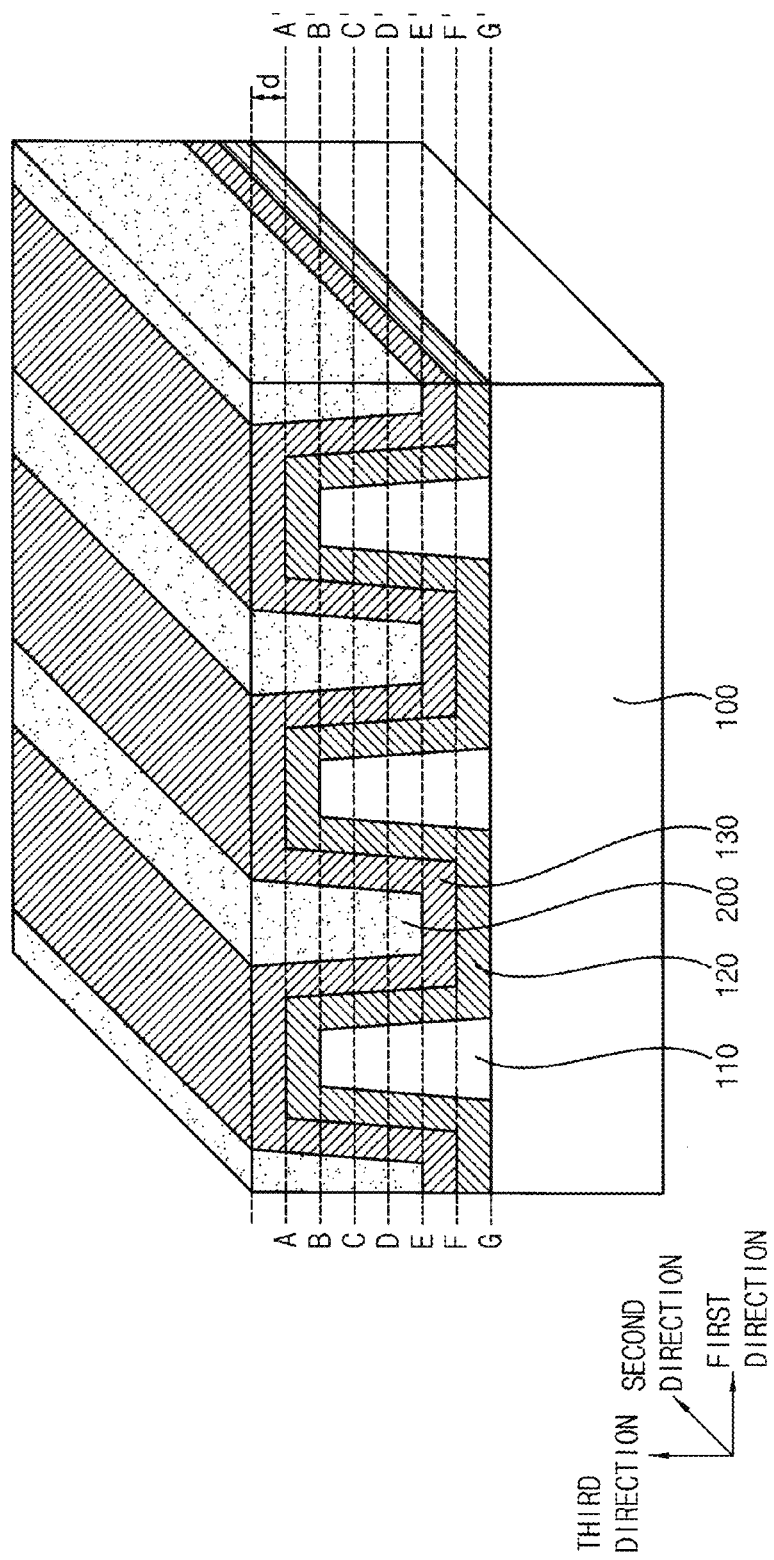
FIG. 7 is a perspective view illustrating stages of ion beam milling on a semiconductor structure.
Figure 8:
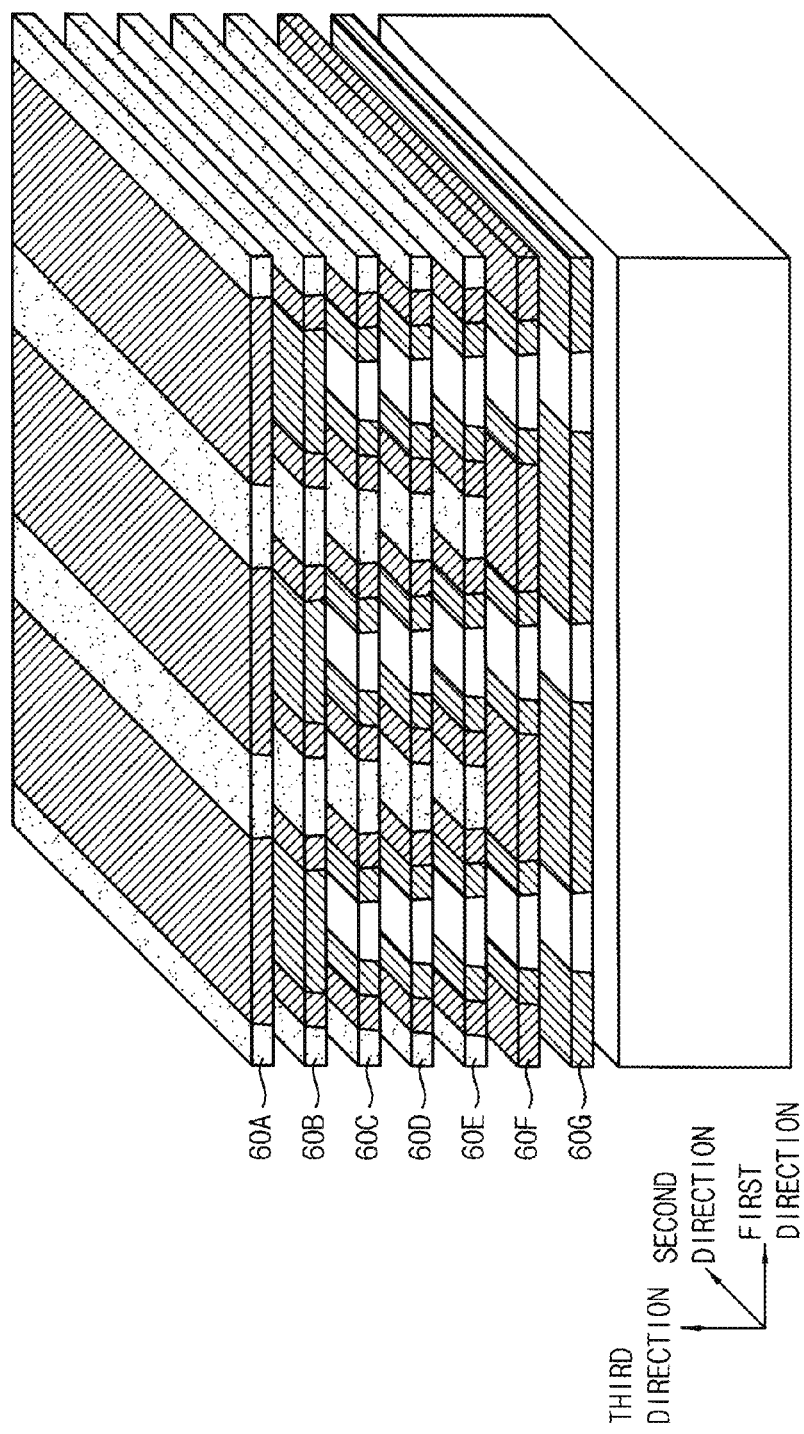
FIG. 8 is a perspective view illustrating 2D spatial/elemental images obtained by the stages of ion beam milling of FIG. 7.
Figure 9:
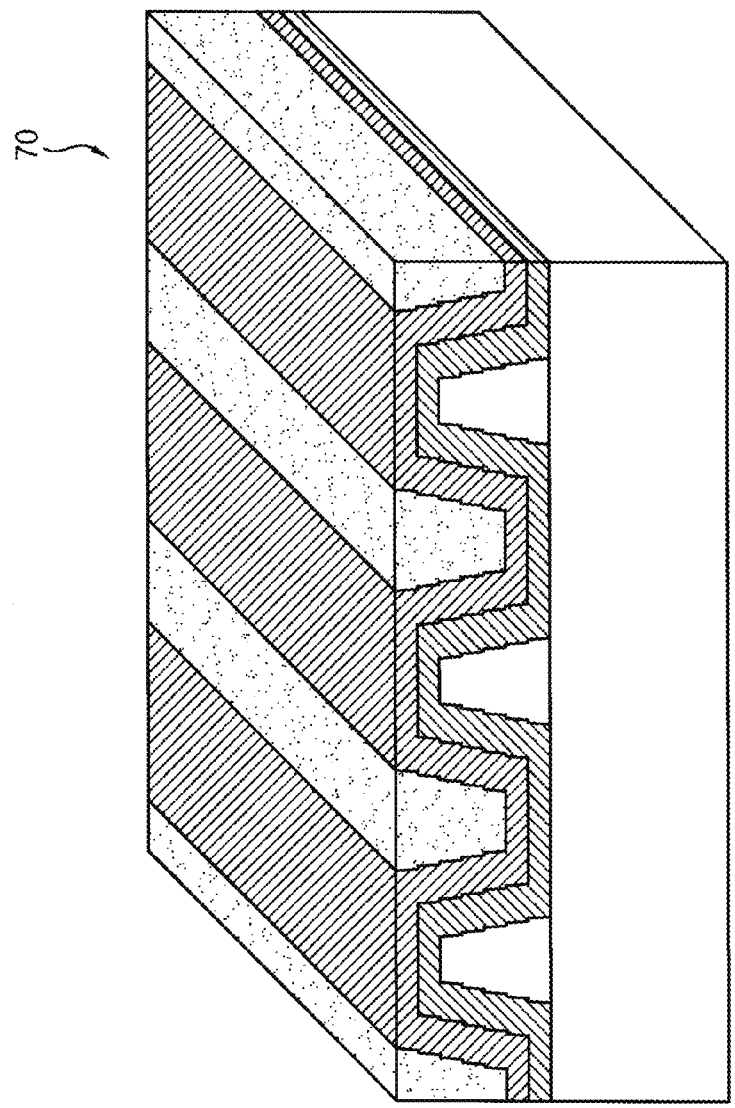
FIG. 9 is a perspective view illustrating a 3D spatial/elemental image reconstructed from the 2D spatial/elemental images of FIG. 8.

FIG. 6 is a flow chart illustrating an image creating method in accordance with some example embodiments. FIG. 7 is a perspective view illustrating stages of ion beam milling on a semiconductor structure. FIG. 8 is a perspective view illustrating 2D spatial/elemental images obtained by the stages of ion beam milling of FIG. 7. FIG. 9 is a perspective view illustrating a 3D spatial/elemental image reconstructed from the 2D spatial/elemental images of FIG. 8.

Referring to FIGS. 6 to 9, ion milling may be repeatedly performed on a surface of a sample in a depth direction to obtain elemental images from the milled surfaces respectively (S100) and spatial images may be obtained from the sample surfaces respectively (S110).

First, a sample having a multi-layered structure of a plurality of stacked layers may be prepared. The multi-layered structure may be formed by semiconductor manufacturing processes for manufacturing semiconductor devices such as DRAM, VNAND, etc.

As illustrated in FIG. 7, a multi-layered structure may be formed on a silicon substrate 100 by semiconductor manufacturing processes. The multi-layered structure may include a structure 110 extending in a direction on the substrate 100 and first and second layers 120 and 130 covering the structure 110. A plurality of the structures 110 may be spaced apart from each other in a first direction, and the structure 110 may extend in a second direction perpendicular to the first direction. The first and second layers may include an insulation layer, a dielectric layer, a metal layer, etc.

Then, an electron beam may be irradiated on a surface of the multi-layered structure on the substrate 100, and then secondary electrons emitted from the surface may be detected to obtain a SEM image. In here, X-rays emitted from the surface of the multi-layered structure may be detected using EDX to obtain an elemental image.

Then, an ion beam may be irradiated on the surface of the multi-layered structure to perform ion milling to a predetermined depth (d), and then secondary ions emitted from the ion milled surface may be detected to obtain an elemental image. For example, the ion milling may be performed using focused ion beam (FIB) or cluster ion beam (CIB).

In some example embodiments, before performing the ion milling, a protection layer 200 may be formed to fill gaps between patterns of the multi-layered structure. The protection layer may be formed by an ion beam induced deposition process. Additionally, an ion beam marker may be formed in a region of interest (ROI) to be used for an image matching in a following image reconstruction stage.

The ion milling may be repeatedly performed to form cross-sections (A-A' cross-section to G-G' cross-section) along a depth direction (third direction). A spatial image and an elemental image may be obtained from each of the milled surfaces.

The spatial image may be a SEM image. Additionally, a GSD image together with the SEM image may be used as the spatial image to provide 2D spatial information of the pattern formed on the surface of the substrate 100. The elemental image may be a chemical characterization image obtained by SIMS or EDX to provide material information of the milled surface. The spatial image may have a first resolution, and the elemental image may have a second resolution lower than the first resolution. The spatial image may be a black and white image, and the elemental image may be a black and white image or a color image.

Then, the spatial image and the elemental image at each depth along the depth direction of the sample may be composed to form a plurality of 2D spatial/elemental images (S120), and the 2D spatial/elemental images at vertical depths may be reconstructed to form a 3D spatial/elemental image 70 (S140).

As illustrated in FIG. 8, the spatial image of a relatively high resolution and the elemental image of a relatively low resolution from each of the milled surfaces along the depth direction (A-A' cross-section to G-G' cross-section) may be composed to high-resolution 2D spatial/elemental images (60A to 60G). Accordingly, the spatial image may compensate the low resolution of the elemental image.

Then, as illustrated in FIG. 9, the 2D spatial/elemental images may be reconstructed to form the 3D spatial/elemental image 70.

In some example embodiments, 2D (lateral) resolution of an element mapping image may be compensated and improved by composition with a high-resolution spatial image, and reconstructed into a 3D structural material image, to perform on-cell monitoring of in-line semiconductor process.

Accordingly, because the spatial/elemental image may include an elemental image obtained by SIMS or EDX, a chemical defect, which is not seen in the spatial image such as SEM image, may be detected.

Some example embodiments may be applied to an in-line process monitoring of semiconductor processes for manufacturing various types of semiconductor devices including upper and lower pattern structures, e.g., pads, contact holes, masks, wirings, etc. For example, the methods may be applied to a process monitoring of processes for manufacturing a semiconductor device such as the above-mentioned DRAM device as well as FLASH or logic device.

The foregoing is illustrative of example embodiments and is not to be construed as limiting thereof. Although a few example embodiments have been described, those skilled in the art will readily appreciate that many modifications are possible in example embodiments without materially departing from the novel teachings and advantages. Accordingly, all such modifications are intended to be included within the scope of example embodiments as defined in the claims. In the claims, means-plus-function clauses are intended to cover the structures described herein as performing the recited function and not only structural equivalents but also equivalent structures. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. An image creating method, comprising:
obtaining a spatial image having 2D spatial information from a surface of a sample;
milling the surface of the sample to obtain an elemental image having material information from the milled surface; and
composing the spatial image and the elemental image to form a 2D spatial/elemental image.

2. The image creating method of claim 1, further comprising:
repeatedly performing the milling along a depth direction of the sample;
obtaining the 2D spatial/elemental images with respect to the milled surfaces respectively; and
reconstructing the 2D spatial/elemental images to form a 3D spatial/elemental image.

3. The image creating method of claim 1, wherein the obtaining comprises:
irradiating an electron beam onto the sample surface; and
detecting secondary electrons emitted from the sample surface.

4. The image creating method of claim 3, wherein the obtaining is performed by scanning electron microscope (SEM).

5. The image creating method of claim 3, wherein the obtaining further comprises:
obtaining a design image of the sample.

6. The image creating method of claim 3, wherein the obtaining further comprises:
obtaining an elemental image from the sample surface by using energy dispersive X-ray spectroscopy (EDX).

7. The image creating method of claim 1, wherein the milling comprises:
irradiating an ion beam onto the sample surface; and
detecting secondary ions emitted from the sample surface.

8. The image creating method of claim 7, wherein the milling is performed using focused ion beam (FIB) or cluster ion beam (CIB).

9. The image creating method of claim 1, wherein the spatial image has a first resolution and the elemental image has a second resolution lower than the first resolution.

10. The image creating method of claim 1, wherein the sample comprises a wafer having a multi-layered structure formed thereon.

11. An image creating method, comprising:
repeatedly performing ion milling on a surface of a sample along a depth direction to obtain elemental images from the milled surfaces respectively;
irradiating an electron beam on the surfaces to obtaining spatial images, respectively;

composing the spatial images and the elemental images along the depth direction to form a plurality of 2D spatial/elemental images; and reconstructing the 2D spatial/elemental images to form a 3D spatial/elemental image.

12. The image creating method of claim 11, wherein the irradiating is performed by a scanning electron microscope (SEM).

13. The image creating method of claim 11, wherein the irradiating further comprises:

obtaining an elemental image from the sample surface by using energy dispersive X-ray spectroscopy (EDX).

14. The image creating method of claim 11, wherein the ion milling is performed using focused ion beam (FIB) or cluster ion beam (CIB).

15. The image creating method of claim 11, wherein the spatial image has a first resolution and the elemental image has a second resolution lower than the first resolution.

16. An image creating method, comprising:

ion milling a surface of a sample to obtain an elemental image from the milled surface;

irradiating an electron beam on the surface to obtaining a spatial image;

composing the spatial image and the elemental image along a depth direction to form a 2D spatial/elemental image; and reconstructing the 2D spatial/elemental image to form a 3D spatial/elemental image.

17. The image creating method of claim 16, wherein the irradiating is performed by a scanning electron microscope (SEM).

18. The image creating method of claim 16, wherein the irradiating further comprises:

obtaining an elemental image from the sample surface using energy dispersive X-ray spectroscopy (EDX).

19. The image creating method of claim 16, wherein the ion milling is performed using focused ion beam (FIB) or cluster ion beam (CIB).

20. The image creating method of claim 16, wherein the spatial image has a first resolution and the elemental image has a second resolution lower than the first resolution.

* * * * *